United States Patent [19]

Koepff et al.

[11] Patent Number: 4,992,100
[45] Date of Patent: Feb. 12, 1991

[54] GELATINE GRANULES AS WELL AS METHODS AND APPARATUS FOR THEIR MANUFACTURE

[75] Inventors: Peter Koepff, Heidelberg; Klaus Bräumer, Eberbach; Helmuth Stahl, Michelstadt, all of Fed. Rep. of Germany

[73] Assignee: Deutsche Gelatine-Fabriken Stoess & Co. GmbH, Eberbach, Fed. Rep. of Germany

[21] Appl. No.: 390,653

[22] Filed: Aug. 7, 1989

[30] Foreign Application Priority Data

Aug. 10, 1988 [DE] Fed. Rep. of Germany ....... 3827061

[51] Int. Cl.$^5$ .............................................. C08L 89/00
[52] U.S. Cl. ................................... 106/125; 106/126; 106/130
[58] Field of Search ...................... 106/125, 126, 130

[56] References Cited

U.S. PATENT DOCUMENTS

| | | | |
|---|---|---|---|
| 4,002,485 | 1/1977 | Hammer et al. | 106/136 |
| 4,045,239 | 8/1977 | Hammer et al. | 106/136 X |
| 4,655,840 | 4/1987 | Wittwer et al. | 106/125 X |

FOREIGN PATENT DOCUMENTS 0090600 10/1983 European Pat. Off.
3827061 8/1988 Fed. Rep. of Germany.

*Primary Examiner*—Karl Group
*Attorney, Agent, or Firm*—Shenier & O'Connor

[57] ABSTRACT

Gelatine granules obtained by plasticizing conventional gelatine consist of solid gelatine particles with a water content of from 1 to 12% by weight, with a particle size of from 0.1 to 10 mm, with an entrapped air content of less than 1% by volume and with a melt flow index greater than 1 g/10 min at 110 degrees C. The granules are thermoplastic and solid or hollow molded articles can be made from them like from conventional plastics by extrusion, injection molding, blow molding and the like.

17 Claims, No Drawings

GELATINE GRANULES AS WELL AS METHODS AND APPARATUS FOR THEIR MANUFACTURE

The invention relates to gelatine granules as well as to methods and apparatus for their manufacture.

As is generally known, in all processing on a technical scale, gelatine which usually exists in the form of gelatine powder or gelatine hydrolysate, must be subjected to a dissolving process in water and the relatively large amount of water required then has to be extracted again from the end product that is to be manufactured by gentle drying. All this involves high expenditure with respect to apparatus and energy. In addition, the gelatine end product contains entrapped air bubbles which are released during the dissolving process. In order to remove the air bubbles, it is necessary to degas the gelatine solution prior to further processing, which involves further expenditure with respect to apparatus and time. Technical problems also arise from the extensive shrinkage that occurs during the drying of the gelatine product Fabrication of molded articles consisting of gelatine or gelatine hydrolysate with a molecular weight of less than 10 kD (kilodaltons) is impossible.

It has also been proposed that molded articles be made from gelatine which has been pretreated in the manner described above, i.e., in particular, with water, by extrusion, injection molding and thermoforming (EP-PS 90 600) but so far industrial application of these methods on a larger scale has not been possible. One reason for this is presumably the fact that the gelatine has to be dissolved in water, i.e., presoaked, and the mixture cannot be kept for a longer period of time. In addition, the presoaked material cannot be melted in the conventional screw extruder without the formation of fisheyes (homogeneously). Problems also arise in connection with the metering of the material into the extruder, and, above all, the previously admixed water has to be removed from the end product again by drying.

The object underlying the invention is to eliminate the above-described deficiencies in the manufacture of molded gelatine products and, in particular, to propose a new gelatine starting material which permits processing like a thermoplastic in extruders and similar machines, as used in the plastics industry.

The object is accomplished, in accordance with the invention, by gelatine granules comprising solid gelatine particles with a water content of from 1 to 12% by weight, a particle size of from 0.1 mm to 10 mm, with an entrapped air content of less than 1% by volume and with a melt flow index greater than 1 g/10 min at 110 degrees C. testing temperature, 30 kg total loading weight and using a standard die in accordance with DIN (German standard) A 53 735, page 2 with a length-to-diameter ratio of 8 mm to 2 mm.

The processing of these gelatine granules is carried out with that final water content which the molded products manufactured by plasticization of the granules have. Presoaking of the gelatine granules in water is not necessary. Subsequent drying is also eliminated. The manufacture of molded articles, foams, films, etc. using the inventive gelatine granules takes—exactly as with conventional thermoplastics—only a few seconds as the processing is carried out with the melt and not with the solution. The gelatine granules according to the invention, therefore, behave like a thermoplastic.

The shrinkage of the molded articles manufactured with the gelatine granules is very slight and is settable via additives, for example, plasticizers.

The following description of preferred embodiments serves in conjunction with the Examples given below to explain the invention in further detail.

In accordance with the invention, thermoplastic gelatine granules are manufactured in the following manner: Commercially available gelatine powder and/or commercially available gelatine hydrolysate in powder form is used as starting material. In both cases, the water content may lie between 1 and 12% by weight, preferably between 8 and 12% by weight. The starting material is fed without preconditioning into an extruder, preferably a twin screw extruder with screws rotating in the same direction, with a length-to-diameter (L:D) ratio of at least 35. If required, 0.1 to 80% by weight additives, in particular, plasticizers (1 to 50% by weight), cross-linking agents or hardeners (0.1 to 10% by weight), fillers (0 to 80% by weight) and/or coloring matter (0.001 to 5% by weight) may be admixed with the starting material at special metering locations.

The following are, for example, suitable as plasticizers: glycerol, mannitol, sorbitol, fat, fatty acid, soap, modified or natural starch, ethylene glycol, polyethylene glycol, monoglycerol acetate, diglycerol acetate, triglycerol acetate, fatty acid ester of sugar, water, dimethylene sulfoxide, 2,2,2-trifluoroethanol and/or propylene glycol.

The plasticizer may, in particular, be in the amount of from 5 to 30% by weight, preferably from 5 to 10% by weight.

The following are suitable as crosslinking agents (hardeners) which may be added in the approximate amount of from 0.5 to 5% by weight: aldehyde, dialdehyde, molecules with multiple aldehyde function, diisocyanate, dialdehyde starch, acrylic acid, acrylate, hexamethylene diamine, styrene, reactive melamine derivative and/or acrolein.

The amount of fillers added may be from 20 to 60% by weight, preferably from 30 to 50% by weight. The following are of primary suitability: calcium carbonate, pulp meal (ground wood meal, cotton or the like), carbohydrate (starch and/or sugar), dicalcium phosphate, very finely ground meat meal or bone meal, fish meal, milk protein, soybean flour, fat, fatty acid, polyvinyl alcohol, talcum, polyethylene, polypropylene, polyamide and/or polyester.

The coloring matter may be added in the amount of between 0.1 and 3% by weight, preferably between 0.5 and 2% by weight.

The starting material is plasticized with or without additives in the extruder for a period of time of from 5 seconds to 30 minutes at a temperature of between 30 and 200 degrees C. Depending on the quality of the starting mixture, plasticizing times of between 0.5 and 10 minutes or between 1 and 5 minutes may be adequate. Suitable operating temperatures lie in the ranges of between 5 and 150 degrees C. or from 70 to 130 degrees C.

During the plasticizing, a pressure of between 1 and 300 bar, preferably from 3 to 100 bar or from 5 to 50 bar is exerted on the material.

Endless strands are extruded via one or several dies, preferably round-section dies, provided on the extruder and after cooling-down in an air current are granulated by granulators or strand granulators (as is customary with plastics material) to the same or different particle size. The particle size may lie between 0.1 and 10 mm. The lower limit for the particle size is preferably 1 or 2 mm.

What is surprising in this method of manufacture is that, for example, gelatine powder can be processed in the extruder without preconditioning and that extrudates with a high additive content can be produced without fisheyes.

Owing to the plasticizing of the starting material under pressure and with the use of shear forces in the screw extruder and to the stabilization and shaping at temperatures above the glass transformation point or the melting point of the starting gelatine, all of the protein molecules of the gelatine remain in a lower ordered state after the cooling-down, i.e., the gelatine granules obtained are substantially amorphous, which is provable by crystal structure analysis using X-rays or by thermal analysis. This structure of the granules results in a lowering of the melting point of the gelatine and hence in lower processing temperatures, for example, in an extruder in which an end product is subsequently fabricated from the granules. Owing to the lower ordered state of the gelatine granules obtained by plasticizing conventional gelatine in comparison with dried, commercially available gelatine which is characterized by a high, partially crystalline ordered state, the subsequent shaping on conventional machines for processing thermoplastics is simpler and can be carried out at distinctly lower temperatures—presupposing the same water content.

The lower melting point of the amorphous gelatine granules manufactured in accordance with the invention is a distinct differentiating feature over commercially available gelatine which has a substantially higher melting point. The melting point can be further reduced by mixing a plasticizer homogeneously into the gelatine granules.

Depending on the composition of the gelatine granules, melting points within the range of from 50 to 80 degrees C. are readily achievable.

A further important parameter in distinguishing the gelatine granules according to the invention from conventional gelatine (gelatine powder, gelatine hydrolysate) is the so-called melt flow index, i.e., a quantity used to identify the flow behavior of thermoplastics.

In conjunction with the invention, the melt flow index (MFI) is determined in accordance with the DIN (German standard) 53 435 regulation: A testing cylinder with a piston is used. The cylinder is filled with gelatine granules and a certain quantity of molten granules is expelled at a certain temperature, with a certain loading of the piston and at certain time intervals from a die which is connected to the testing cylinder. The length and diameter of the die are in the ratio of 8 mm to 2 mm. Reference is made, in this connection, to the DIN regulation mentioned above.

The thus measured melt flow index of the gelatine granules according to the invention lies above 1 g/10 min at 110 degrees C. testing temperature, 30 kg total loading weight and using a standard die in accordance with DIN (German standard) A 53 735, page 2 with a length-to-diameter ratio of 8 mm to 2 mm.

In comparison with this, the melt flow index of commercially available gelatine lies practically at zero as gelatine (or gelatine hydrolysate) does not exhibit the flow behavior of thermoplastics. Concrete values of the melt flow index of gelatine granules according to the invention are to be found in the Examples given below.

A further feature of the gelatine granules according to the invention which clearly distinguishes them from conventional gelatine or conventional gelatine hydrolysate is that the granules melt and/or swell up in an electromagnetic microwave field (of, for example, 2450 MHz), an effect which is also capable of industrial application.

Conventional gelatine powder or gelatine hydrolysate in powder form do not exhibit this surprising effect.

In the processing of presoaked gelatine, i.e., which has been treated with water, for the fabrication of molded articles, it is also difficult to achieve an homogeneous distribution of the additives, in particular, the fillers, especially when the fillers are insoluble in water or in plasticizer. In the manufacture of the gelatine granules according to the invention, however, there is an overall even, homogeneous distribution of the additives, in particular, the fillers in the gelatine particles of the granular material because uniform intermixing is carried out in the course of the plasticizing of the starting material in the extruder and separation of the components, as can occur in a presoaked gelatine mixture, is impossible in the performance of the method according to the invention.

Major advantages of the gelatine granules according to the invention are: The manufacture is carried out, as described above, in an extremely simple manner by plasticizing conventional gelatine using heat, pressure and shear force. Also, in particular, a gelatine with a low bloom value may be used as raw material.

The granule components, in particular, the additives, are worked into the melt and so a very homogeneous distribution of all supplementary substances including the undissolved fillers, is achieved. Conditioning is not required in the processing, i.e, in particular, soaking of the starting material with water or degassing by allowing the starting material to stand for some time do not take place. The manufacture is also independent of the level of humidity of the room.

The person concerned with the final processing of the granules, i.e., the manufacturer of molded articles consisting of gelatine, for example, capsules, films, gum candy, receives finished gelatine granules of consistent composition which contain all supplementary substances and can be kept like conventional plastic granules without pretreatment for an unlimited time and which can be processed in a simple manner by, for example, being directly fed into an injection molding machine. Supplementary machines, for example, mixers, air conditioning equipment, driers and the like are not required for the manufacture of the molded end products.

It is possible to work with the gelatine granules without producing any waste, i.e., waste such as, for example, gate marks or the like can be directly circulated in the injection molding machine or the like.

The granules can have a higher content of supplementary substances (solids with different granular geometry and density) than conventional gelatine. In particular, processing without additional water is possible.

EXAMPLE 1

Commercially available gelatine powder with a gelatine firmness of 170 bloom and a water content of 10.6% by weight was metered into the feed opening of a twin screw extruder with two screws driven in the same direction, a screw diameter of 25 mm and a process length L of 48 D (48 times the screw diameter). The metered amount was 5.0 kg/h.

At another location on the extruder cylinder, provided with a further inlet and a non-return valve, glycerol was pumped into the extruder as plasticizer in an amount of 500 g/h.

The mixture was plasticized in the extruder, with the temperature of the cylinder heating zones being set at approximately 100 degrees C. The plasticized material was extruded at a pressure of 100 bar through a round-section die with six bores of 2.0 mm diameter each. The cooled-down, endless strands were granulated in a conventional granulator. The granules obtained thereby can be kept and can be processed on all conventional machines for processing thermoplastics such as injection molding machines, extruders, etc.

The granules consisted of solid gelatine particles with practically no entrapped air (less than 1% by volume), with a particle size of approximately 2 mm and with a melt flow index of 40 g/10 min.

EXAMPLE 2

Commercially available bone gelatine in powder form with the following quality features was used as starting material:

| | |
|---|---|
| bloom value = | 43 g |
| viscosity = | 37 mP (10% aqueous solution at 60 degrees C.) |
| water content = | 11.9% by weight |

The gelatine was metered with its commercially customary moisture (11.9% by weight) without further preconditioning into the feed opening of a twin screw extruder with screws rotating in the same direction. The metered amount was 7.5 kg/h. The extruder had a screw diameter of 25 mm and a process length of 35 D. The operating temperature was 100 degrees C.

Sorbitol was added as plasticizing agent in an amount of 1.875 kg/h through a further opening in the extruder.

The plasticized material was extruded at a pressure of 20 bar through a perforated die with four bores of 2.5 mm diameter each, cooled down and granulated by a strand granulator.

Granules similar to those of Example 1 were obtained but their melt flow index under the same conditions was more than 100 g/10 min.

EXAMPLE 3

4.4 kg/h commercially available gelatine powder was metered into the feed opening of a twin screw extruder with two screws driven in the same direction and a screw diameter of 25 mm. The process length of the extruder was 48 D. The physical data of the gelatine were as follows:

| | |
|---|---|
| bloom value = | 161 g |
| viscosity = | 71 mP (10% aqueous solution at 60 degrees C.) |
| pH value = | 5.5 |
| water content = | 11.7% by weight |

800 g/h glycerol as plasticizer was metered into the extruder at another metering location.

Commercially available potato starch was added in an amount of 2.8 kg/h.

The material was plasticized in the extruder at 100 degrees C.

After extrusion through a flat film die with a width of 130 mm, which was vertically adjustable between 0.1 and 0.5 mm, granulation was carried out with a granulator.

The granules obtained thereby were capable of being kept without subsequent treatment and it was possible for molded articles to be fabricated from them without further additives in a conventional injection molding machine.

Under the testing conditions indicated above, the granules had a melt flow index of 23 g/10 min.

EXAMPLE 4

Commercially available gelatine powder with a bloom value of about 100 and a particle size range of from 0 to 3.0 mm was metered into the extruder in accordance with Example 1. The metering rate was 4.5 kg/h.

450 g/h glycerol was pumped in at another location via a non-return valve. Plasticization was carried out at temperatures of between 85 and 110 degrees C., with respect to several heating zones of the extruder. 2.2 kg/h very finely ground chalk (calcium carbonate) was subsequently added as filler to the plasticized material and uniformly distributed in the melt.

Extrusion was then carried out via round-section dies (diameter 2 mm) at a pressure of 120 bar and granulation was performed with a granulator. Thermoforming sheets were able to be made from the granules obtained thereby without further conditioning on a flat film extrusion line.

EXAMPLE 5

Commercially available gelatine (bloom value 50) was fed into the extruder in accordance with Example 1 in an amount of 4.4 kg/h. 0.4 kg/h glycerol was pumped into the extruder at another metering location. The heating zones of the extruder were heated to temperatures of between 40 and 110 degrees C. The material was plasticized at a screw speed of approximately 100 r.p.m. and a pressure of about 25 bar.

At third and fourth metering locations, each of which was provided with a non-return valve, suspensions of a white color ($TiO_2$) or a red color (iron oxide) were added to the plasticized material at a pumping capacity of 100 g/h.

After extrusion through a die with four bores of 2.5 mm diameter, granulation was carried out. The granules obtained thereby were capable of being kept without subsequent drying or other conditioning and were able to be processed like thermoplastics.

Molded articles in the form of hard capsules were made from the granules on an injection molding machine without any problems and at the first go—in a cycle time of 10 seconds—in a two-plate mold.

The sprue (waste) was granulated, as is customary with thermoplastics, and fed to the injection molding machine again. Multiple recycling of the material was possible without any loss in quality being detected. It was possible to undetachably join the injection molded articles by all welding methods which are customary in the processing of thermoplastics such as, for example, heating reflector welding, ultrasonic welding or high-frequency welding.

The melt flow index of the granules was 60 g/10 min at 100 degrees C.

EXAMPLE 6

The work was performed as in Examples 1 to 5, but instead of gelatine powder, gelatine hydrolysate with a mean molecular weight of about 3000 daltons was metered into the extruder. Gelatine granules with the properties given in Examples 1 to 5 were obtained and were capable of being further processed in the same way as indicated therein.

EXAMPLE 7

1.0 kg/h commercially available gelatine powder with a bloom value of 300 was metered into the extruder in accordance with Example 1. At another metering location, liquid protein hydrolysate with a dry substance content of 60% by weight was pumped into the extruder in an amount of 5.0 kg/h. 0.3 kg/h glycerol was pumped in at a third metering location. The material was plasticized, with the temperature of the heating zones of the screw cylinder being kept at between 40 and 135 degrees C.

The excess water was removed by the application of vacuum to one of the cylinder zones of the extruder.

The thus obtained thermoplastic material was extruded via a round-section die with four bores of 2.5 mm diameter each and subsequently granulated.

The thermoplastic gelatine granules which were capable of being kept had a water content of 10.0% by weight.

Solid molded articles, for example, rolls and bags were made from the granules on an injection molding machine. Clear gelatine films free from streaks and fisheyes were made from another portion of the granules on a single screw extruder via a flat film die.

EXAMPLE 8

Several samples of the geltine granules according to the invention (with and without plasticizer) were placed together with several samples of conventional gelatine and gelatine hydrolysate for 7 minutes in a commercially available microwave oven (2450 MHz). All of the samples of the granules swelled up to a considerable degree. The gelatine and gelatine hydrolysate samples showed no reaction.

This effect was made use of in the manufacture of snacks for diabetics from the gelatine granules according to the invention.

EXAMPLE 9

The same procedure as described in Examples 1 and 2 was carried out. However, the metered amount of plasticizing agent (glycerol, sorbitol and the like) was increased such that with a total material flow rate of 5.0 kg/h, glycerol was added in the amount of 500 g/h at the first metering location and sorbitol in the amount of 750 g/h at the second metering location. Hence the total content of plasticizer in relation to the total material was 25 % by weight.

The granules obtained with this method were suitable, above all, for manufacturing blown films and for the fabrication of sealable flat film tapes from which soft gelatine capsules can, in turn, be made.

Under the conditions mentioned above, the granules had a melt flow index of 110 g/10 min.

EXAMPLE 10

This Example relates to the recycling of waste.

Ground sprues from injection molding tests in accordance with the Examples given above and ground waste from injection blow molding tests, flat film tests and granule tests having on average a plasticizer content of 9% were metered into the extruder in accordance with Example 1 in an amount of 5.0 kg/h. The material was readily plasticizable in the extruder.

A suspension (1:1) of iron oxide in an amount of 100 g/h was pumped into the plasticized material by metering pumps and a 1% suspension of titanium dioxide in glycerol in an amount of 1.1 kg/h at a further metering location. The total content of glycerol in the mixture was approximately 25% by weight in relation to the extruded granules.

Calcium stearate in an amount of 1% in relation to the total material was added at another metering location.

The regenerated granular material was very well suited for the fabrication of blown films.

During the processing of the granules in an extruder with two counter-rotating twin screws, air or another gas, for example, $CO_2$ can be intermixed such that a foamed strip is extrudable.

EXAMPLE 11

Commercially available cooking gelatine (bloom value approximately 60, water content 9.5% by weight) was fed into the feed opening of the twin screw extruder in accordance with Example 1 in an amount of 4.0 kg/h. At the same time, magnesium stearate was added in the amount of 50 g/h. Glycerol in the amount of 1.0 kg/h was pumped into the extruder at another metering location.

As described in Example 1, the material was plasticized for 3 minutes.

The plasticized material was extruded at a material temperature of 120 degrees C. via a sheet die (slot width 130 mm, slot height 1.0 mm). After cooling-down of the extruded strip, the thermoplastic material was granulated by a granulator.

Molded articles were manufactured from a portion of these granules on an injection molding machine. From another portion of the granules, flat films were extruded with a single screw extruder having a flat film die arranged at its outlet opening and were calibrated by a calender connected at its outlet side. Molded articles were manufactured from these sheet-shaped, flat films on a conventional vacuum thermoforming machine.

EXAMPLE 12

Gelatine of inferior quality in the form of animal glue (bone and skin glue) was plasticized and granulated as described in Example 2.

The granules had a water content of 8.5%. They were plasticized in a conventional film calendering line and made into tapes. The tapes were directly usable as hot melt adhesives.

EXAMPLE 13

From the gelatine granules which had been manufactured in accordance with one of the methods described in the Examples given above, tubes with a threaded head were blown on automatic injection blow molding machines.

The composition of the granules was as follows:

| | |
|---|---|
| gelatine (bloom value 160) = | 65% by weight |
| sorbitol = | 25% by weight |

-continued

| | |
|---|---|
| water = | 10% by weight |
| | 100% by weight |

The granules were plasticized on a conventional automatic injection blow molding machine of the type Duo 30 at 100 degrees C. and extruded and tubes were blown via a twin die head. The cycle time was 7 seconds. The fabricated tubes had the following dimensions:

| | |
|---|---|
| length = | 70 mm |
| external diameter = | 15 mm |
| wall thickness = | 1 mm |
| thread length = | 5 mm |

EXAMPLE 14

In the manufacture of blown films, gelatine granules manufactured as described in the Examples given above, with the following composition, were used as starting material:

| | |
|---|---|
| gelatine with a bloom value of 164 = | 64% by weight |
| water = | 10% by weight |
| glycerol = | 25% by weight |
| magnesium stearate = | 1% by weight |
| | 100% by weight |

The granules were plasticized in an extruder at between 110 and 120 degrees C. and extruded via a tubular film die with a diameter of 30 mm. The tube had a wall thickness of 0.05 mm. By introducing blowing air, the tube diameter was increased by a multiple and the thickness of the film thus set.

The material was very well suited for the fabrication of tubular films. The stretchability and the stability of the extrudate were so good that the thickness of the films was variable within a wide range.

EXAMPLE 15

Example 14 was repeated with the same results, but the gelatine granules contained 30% by weight of modified cornstarch as filler.

EXAMPLE 16

Commercially available gelatine powder with a gelatine firmness of 84 bloom, a viscosity of 4 mPa/sec. (measured at 60 degrees C. in 10% solution), a pH value of 5.5 and a water content of 10.2% by weight was metered into the feed opening of a twin screw extruder with two screws driven in the same direction, a screw diameter of 25 mm and a process length L of 48 D (48 times the screw diameter).

The metered amount was 1.6 kg/h. At the same time, polyethylene in powder form was metered into the feed opening of the extruder in an amount of 6.32 kg/h.

At another location on the extruder, which was provided with a further inlet and a non-return valve, glycerol was pumped into the extruder as plasticizer in an amount of 80 g/h.

The mixture was plasticized in the extruder, with the temperature of the cylinder heating zones being set increasingly from 60 to 115 degrees C. The plasticized material was extruded under a pressure of 35 bar through a round-section die with 6 bores of 2.0 mm diameter each. The cooled-down, endless strands were granulated in a conventional granulator.

The granules obtained thereby were capable of being kept and had a water content of 2.0% by weight. Discs of 50 mm diameter with an average thickness of 4 mm were fabricated therefrom on a conventional injection molding machine.

The heating zones of the injection molding machine were set at from 110 to 130 degrees C. The specific injection pressure was approximately 1800 bar. The cycle time was approximately 4 seconds.

The melt flow index of the granules was greater than 10 g/10 min.

EXAMPLE 17

The procedure was essentially the same as in Example 16.

The following mixture was metered into the feed opening of the extruder in an amount of 7.5 kg/h:

| | |
|---|---|
| 42.5% | gelatine (84 bloom, 10.2% water) |
| 42.5% | polyethylene |
| 7.5% | calcium carbonate |
| 2.0% | titanium dioxide |
| 5.0% | sorbitol |
| 0.5% | emulsifier |
| 100.0% | |

The heating zones of the extruder were set at temperatures between 55 and 110 degrees C.

Granules with a water content of 4.4% by weight were obtained.

Molded articles were fabricated from these granules on an injection molding machine.

The melt flow index of the granules was greater than 10 g/10 min.

It was found that granules with the same properties are also obtainable from other biopolymers as well as from gelatine using the methods described above, i.e., granules which are manufactured by simple plasticization of the starting material and are suitable for the fabrication of molded articles by means of extrusion, injection molding or the like. Manufacture and use of these biopolymer granules are included within the scope of the description, in particular, the Examples given above.

Suitable biopolymers are, in particular, starch, other protein hydrolysates, animal glue, all animal and plant proteins as well as hydrocolloids, for example, polysaccharides, guar meal, xanthene, etc.

All of the properties and measures indicated above with reference to gelatine are substantially and readily transferable to other biopolymers. Hence plasticizable biopolymers which are capable of being kept and from which solid or hollow molded articles can be fabricated on all standard machines for processing thermoplastics, for example, injection molding, extrusion, thermoforming and pressure forming machines, as described above in conjunction with gelatine, are available in granular form by application of the invention.

In particular, fresh bone, degreased bone scrap, osseine, pork rind, comminuted cow or calf skin are suitable as starting materials for protein granules The starting material is fed with the usual additives, if desired, together with an enzyme, into the extruder and plasticized using pressure, raised temperature and shear force. The plasticized material is extruded and the extrudate granulated.

The present disclosure relates to the subject matter disclosed in German application No. P 38 27 061.7 of Aug. 10, 1988, the entire specification of which is incorporated herein by reference.

We claim:

1. Gelatine granules for use in forming gelatine articles by means of a plastics extruder without presoaking, comprising solid gelatine particles with a water content of from 1 to 12% by weight, with a particle size of from 0.1 to 10 mm, with an entrapped air content of less than 1% by volume and with a melt flow index (MFI) greater than 1 g/10 min at 110 degrees C. testing temperature, 30 kg total loading weight and using a standard die in accordance with DIN (German standard) A 53 735, page 2 with a length-to-diameter ratio of 8 mm of 2 mm.

2. Gelatine granules according to claim 1, characterized by a water content of from 8 to 12% by weight.

3. Gelatine granules according to claim 1, characterized by an additive content of from 0.1 to 80% by weight.

4. Gelatine granules according to claim 3, characterized by a plasticizer content of from 1 to 50% by weight.

5. Gelatine granules according to claim 4, characterized by a plasticizer content of from 5 to 30% by weight.

6. Gelatine granules according to claim 4, characterized by a plasticizer content of from 5 to 10% by weight.

7. Gelatine granules according to claim 4, characterized in that the plasticizer is selected from the group consisting of glycerol, mannitol, sorbitol, a fat, a fatty acid, a soap, a modified starch, natural starch, ethylene glycol, polyethylene glycol, monoglycerol acetate, diglycerol acetate, triglycerol acetate, fatty acid ester of sugar, water, dimethylene sulfoxide, 2,2,2-trifluoroethanol and propylene glycol.

8. Gelatine granules according to claim 3, characterized by a crosslinking agent content of from 0.1 to 10% by weight.

9. Gelatine granules according to claim 8, characterized by a crosslinking agent content of from 0.5 to 5% by weight.

10. Gelatine granules according to claim 8, characterized in that the hardener is selected from the group consisting of an aldehyde, dialdehyde, a molecule with multiple aldehyde function, a diisocyanate, a dialdehyde starch, acrylic acid, acrylate, hexamethylene diamine, styrene, reactive melamine derivative and acrolein.

11. Gelatine granules according to claim 3, characterized by a filler content of from 1 to 80% by weight.

12. Gelatine granules according to claim 11, characterized by a filler content of from 20 to 60% by weight.

13. Gelatine granules according to claim 12, characterized by a filler content of from 30 to 50% by weight.

14. Gelatine granules according to claim 11, characterized in that the filler is selected from the group consisting of calcium carbonate, wood meal, cotton, starch, sugar, dicalcium phosphate, meat meal, bone meal, fish meal, milk protein, soybean flour, fat, fatty acid, polyvinyl alcohol, talcum, polyethylene, polypropylene, polyamide and polyester.

15. Gelatine granules according to claim 1, characterized by a coloring matter content of between 0.001 and 5% by weight.

16. Gelatine granules according to claim 15, characterized by a coloring matter content of between 0.1 and 3% by weight.

17. Gelatine granules according to claim 15, characterized by a coloring matter content of between 0.5 and 2% by weight.

* * * * *

UNITED STATES PATENT AND TRADEMARK OFFICE
CERTIFICATE OF CORRECTION

PATENT NO. : 4,992,100

DATED : February 12, 1991

INVENTOR(S) : Peter Koepff, Klaus Braumer, Helmuth Stahl

It is certified that error appears in the above-identified patent and that said Letters Patent is hereby corrected as shown below:

Column 11, line 18 - "of" should read -- to --.

Signed and Sealed this

Fourth Day of August, 1992

*Attest:*

DOUGLAS B. COMER

*Attesting Officer*      *Acting Commissioner of Patents and Trademarks*